(12) United States Patent
Appelbaum

(10) Patent No.: US 10,653,685 B2
(45) Date of Patent: May 19, 2020

(54) PHARMACEUTICAL COMPOSITIONS AND METHODS FOR THE TREATMENT OF HYPOXIA-RELATED DISEASES

(71) Applicant: Jerachmiel Yori Appelbaum, Jerusalem (IL)

(72) Inventor: Jerachmiel Yori Appelbaum, Jerusalem (IL)

( * ) Notice: Subject to any disclaimer, the term of this patent is extended or adjusted under 35 U.S.C. 154(b) by 0 days.

(21) Appl. No.: 15/755,262

(22) PCT Filed: Sep. 13, 2016

(86) PCT No.: PCT/US2016/051482
§ 371 (c)(1),
(2) Date: Feb. 26, 2018

(87) PCT Pub. No.: WO2017/035542
PCT Pub. Date: Mar. 2, 2017

(65) Prior Publication Data
US 2018/0243276 A1 Aug. 30, 2018

Related U.S. Application Data

(60) Provisional application No. 62/208,914, filed on Aug. 24, 2015.

(51) Int. Cl.

| | | |
|---|---|---|
| *A61K 31/444* | (2006.01) | |
| *A61K 31/4402* | (2006.01) | |
| *A61K 31/44* | (2006.01) | |
| *A61K 9/00* | (2006.01) | |
| *A61P 9/10* | (2006.01) | |
| *A61P 9/00* | (2006.01) | |
| *A61K 31/734* | (2006.01) | |

(52) U.S. Cl.
CPC .......... *A61K 31/444* (2013.01); *A61K 9/0019* (2013.01); *A61K 9/0024* (2013.01); *A61K 31/44* (2013.01); *A61K 31/4402* (2013.01); *A61K 31/734* (2013.01); *A61P 9/00* (2018.01); *A61P 9/10* (2018.01)

(58) Field of Classification Search
None
See application file for complete search history.

(56) References Cited

U.S. PATENT DOCUMENTS

| | | | | |
|---|---|---|---|---|
| 5,082,851 A | * | 1/1992 | Appelbaum | A61K 31/44 514/332 |
| 2007/0027064 A1 | * | 2/2007 | Appelbaum | A61K 31/4402 514/183 |
| 2010/0216739 A1 | * | 8/2010 | Lifshitz | A61K 9/0024 514/54 |
| 2012/0276152 A1 | * | 11/2012 | Hossainy | A61K 45/06 424/400 |

FOREIGN PATENT DOCUMENTS

| | | |
|---|---|---|
| EP | 2136783 B1 | 4/2013 |
| WO | 2004/098669 A1 | 11/2004 |
| WO | 2013003445 A1 | 1/2013 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Wilkinson, G. Pharmacokinetics, The Dynamics of Drug Absorption, Distribution, and Elimination (2001). In: Goodman and Gilman's the pharmacological basis of therapeutics. International edition, 10th edition, Mc Grow Hill, 971. (Year: 2001).*
SodiumAlginate (Excipient—pharmacologicaly inactive ingredient) downloaded Jun. 26, 2019, from drugs.com/inactive/sodium-alginate-268.html.
IK-5001 for the prevention of remodeling of the ventricle and congestive heart failure after acute myocardial infarction (PRESERVATION-1), donwloaded Jun. 27, 2019, from clinicaltrials.gov/ct2/show/NCT01226563?term=ik&rank=3.
Frey et al., Intracoronary Delivery of Injectable Bioabsorbable Scaffold (IK-5001) to Treat Left Ventricular Remodeling After ST-Elevation Myocardial Infarction, Cir Cardiovascular Interventions 7:806-812 (2014).
Shmist et al., N,N,N',N'-Tetrakis(2-pyridylmethyl)-ethylenediamine Improves Myocardial Protection against Ischemia by Modulation of Intracellular Ca2+ Homeostasis, Journal of Pharmacology and Experimental Therapeutics. June, 313(3):1046-1057 (2005).
Appelbaum et al., Tpen, a heavy metal chelator, protect the isolated perfused rat heart from reperfusion-induced arrhythmias, Journal of Molecular and Cellular Cardiology. Aug. 1988. (Abstract).
Appelbaum et al., TPEN, a transition metal chelator, improves myocardial protection during prolonged ischemia, J Heart Lung Transplant.;11(5):979-85. Sep.-Oct. 1992. (Abstract).
Appelbaum et al., Role of nitric oxide and TPEN, a potent metal chelator, in ischaemic and reperfused rat isolated hearts, Clin Exp Pharmacol Physiol 25: 496-502, 1998. (Abstract).
Lian et al., Mars, a novel preservation solution is superior to uw solution in rat cardiac and kidney transplantation models, London, ON,Canada. The Journal of Urology vol. 181, No. 4, Supplement, Apr. 29, 2009.
Shmist et al., TPEN Improves Myocardial Protection against Ischemia by Modulation of Intracellular Ca2+ Homeostasis, American Society for Pharmacology and Experimental Therapeutics, pp. 1-39 (2005) (Downloaded from jpet.aspetjournals.org at ASPET Journals on Mar. 29, 2019).
Yamada et al., Is reperfusion-induced ventricular fibrillation an oxygen-dependent or a flow-dependent phenomenon?, J Mol Cell Cardiol, 20(Supplement V):31 (1998) (Abstract).
Aksnes et al., Mechanism for mycardial potassium uptake after short-lasting myocardial ischemia, Experimental Medial Research, S.29:33 (Abstract).
Sztretye et al., Effect of TPEN on the calcium release of cultured C2C12 mouse myotubes, J Muscle Res Cell Motil, 28:421-428 (2007).

\* cited by examiner

*Primary Examiner* — Dale R Miller
(74) *Attorney, Agent, or Firm* — Browdy and Neimark, PLLC

(57) ABSTRACT

A pharmaceutical composition including N,N,N',N'-tetrakis-(2-pyridylmethyl)-ethylenediamine (TPEN) or a pharmaceutically acceptable salt thereof, an alginate compound, and a pharmaceutically acceptable carrier. The pharmaceutical composition is useful for the treatment of hypoxia-related diseases.

14 Claims, No Drawings

PHARMACEUTICAL COMPOSITIONS AND METHODS FOR THE TREATMENT OF HYPOXIA-RELATED DISEASES

FIELD AND BACKGROUND OF THE INVENTION

The present invention, in some embodiments thereof, relates to pharmaceutical compositions and methods of use thereof for treating hypoxia-related diseases and, more particularly, to pharmaceutical compositions including TPEN and an alginate compound as active ingredients.

Hypoxic-Ischemic injury results from a tissue restriction in blood supply leading to a mismatch between oxygen supply and demand, which may result in cell necrosis. Restoration of oxygenated blood to an ischemic tissue, i.e., reoxygenation, may give rise to a more severe tissue damage which is usually associated with programmed cell death, namely apoptosis. The link between these two events is known as ischemia-reperfusion injury (IRI). Hence minimizing IRI has broad range clinical implications. IRI is regarded as a redox active metal and free radical mediated cascade that occurs during acute myocardial infarction, stroke, thrombolysis, and other pathological situations associated with ischemia followed by reoxygenation/reperfusion. This type of injury/damage to tissue and organs also occurs in the post-ischemic reperfusion during medical procedures such as cardiopulmonary bypass, percutaneous coronary intervention, coronary angioplasty and other thrombolytic procedures.

Biologically important transition-metals, such as copper, iron and zinc, are also redox active metals and have been found to play a critical mediatory role in reperfusion-induced myocardial damage. Hence, their intracellular transport is tightly regulated and under normal physiological conditions, are stored in situ within protective intracellular stores proteins like ferritin and ceruloplasmin.

However, under situations as hypoxia-ischemia they are frequently released from their stores and subjected to high oxygen level upon initiating reperfusion. The result is the triggering of redox-active catalysis processes and formation of harmful free radicals, so called reactive oxygen species (ROS) via the Fenton and Haber-Weiss reactions.

ROS are involved in and mediates many diseases, syndromes and pathologies, such as heart and brain stroke, brain trauma, organs transplants rejection, various neurodegenerative diseases, arthritis, etc.

Ischemia-induced high accumulation of intracellular transition metals as iron, copper and also zinc which significantly contributed to organ injury like ischemic brain damage through promotion of neuronal apoptotic death. Removing zinc by chelating agents may be an effective approach to reduce ischemic brain injury.

U.S. Pat. No. 5,082,851 to the present inventor teaches a metal chelating agent, N,N,N',N'-tetrakis-(2-pyridylmethyl)-ethylenediamine (TPEN), being capable of protecting heart tissue from ischemia-reperfusion damage. This high specificity heavy metal chelating agent is thought to work by changing the redox potential of redox-active metals (transition metals), into an inactive form before the onset of reoxygenation and hence preventing the yield and the release of hazardous reactive oxygen species (ROS).

International patent application WO 2013/003445 teaches that TPEN is capable of providing heart cells up to, but not greater than, 70% protection from hypoxia stress injury. The effective concentration range of TPEN was between about 1 to about 10 μM. TPEN administered at higher concentrations resulted in decreasing protection efficacy (Journal of Muscle Research and Cell Motility, October 2007, Volume 28, issues 7-8, pp. 421-428).

There is thus a widely recognized need for, and it would be highly advantageous to have, pharmaceutical compositions for treating hypoxia-related diseases which are effective and devoid of the above limitations.

SUMMARY OF THE INVENTION

According to one aspect of the present invention there is provided a pharmaceutical composition including TPEN or a pharmaceutically acceptable salt thereof, an alginate compound, and a pharmaceutically acceptable carrier.

According to another aspect of the present invention there is provided a method of treating a hypoxia-related disease. The method includes the step of administering to a subject in need thereof a therapeutically effective amount of the pharmaceutical composition.

According to yet another aspect of the present invention there is provided a method of treating a hypoxia-related disease. The method includes the steps of: (i) administering to a subject in need thereof a therapeutically effective amount of TPEN or a pharmaceutically acceptable salt thereof, and (ii) administering to the subject a therapeutically effective amount of an alginate compound.

According to further features in preferred embodiments of the invention described below the alginate compound is sodium alginate.

According to still further features in the described preferred embodiments the average molecular weight of the alginate compound ranges from about 10 to about 300 kDa.

According to still further features in the described preferred embodiments the average molecular weight of the alginate compound ranges from about 10 to about 50 kDa.

According to still further features in the described preferred embodiments the concentration of the alginate compound in the pharmaceutical composition ranges from about 0.1 to about 10% (w/v).

According to still further features in the described preferred embodiments the concentration of the alginate compound in the pharmaceutical composition ranges from about 1 to about 4% (w/v).

According to still further features in the described preferred embodiments the concentration of the alginate compound in the pharmaceutical composition is about 2% (w/v).

According to still further features in the described preferred embodiments the concentration of the alginate compound in the pharmaceutical composition is about 1% (w/v).

According to still further features in the described preferred embodiments the concentration of the TPEN in the pharmaceutical composition ranges from 0.1 to 100 μM.

According to still further features in the described preferred embodiments the concentration of the TPEN in the pharmaceutical composition is about 1 to 50 μM.

According to still further features in the described preferred embodiments the concentration of the TPEN in the pharmaceutical composition ranges from 1 to 10 μM.

According to still further features in the described preferred embodiments the concentration of the TPEN in the pharmaceutical composition ranges from 3 to 5 μm.

According to still further features in the described preferred embodiments a monomer ratio between α-L-guluronic acid and β-D-mannuronic acid in the alginate compound ranges between 1:1 and 3:1.

According to still further features in the described preferred embodiments the hypoxia-related disease is selected from a group consisting of cardiovascular disease, ischemic heart disease, acute myocardial infarction (AMI), ischemic brain condition, ischemic stroke, macular degeneration, ocular ischemic syndrome, ischemic optic neuropathy, diabetic retinopathy, arthritis, inflammation, sepsis, sepsis-induced shock, renal disease, tissue fibrosis, gastrointestinal disease, neurodegenerative disease, respiratory distress syndrome, bronchopulmonary displasia, pulmonary hypertension, hypoxic pulmonary hypertension, severe pulmonary hypertension, COPD, diabetic retinopathy, diabetes, corneal neovascularization, pathogenic blood vessel growth, musculoskeletal disorder, ischemic-reperfusion injury, myocardial hypoxia, or cardiac hypertrophy.

According to still further features in the described preferred embodiments the heart disease is an ischemic heart disease.

According to still further features in the described preferred embodiments the heart disease is acute myocardial infarction.

According to still further features in the described preferred embodiments the administering is effected via injection or catheterization.

According to still further features in the described preferred embodiments the catheterization is intra-arterial catheterization.

According to still further features in the described preferred embodiments the effective amount ranges from about 0.1 to about 10 ml.

According to still further features in the described preferred embodiments the effective amount ranges from about 0.5 to about 5 ml.

According to still further features in the described preferred embodiments the step of administering TPEN and the step of administering an alginate compound are effected concomitantly.

According to still further features in the described preferred embodiments the step of administering TPEN and the step of administering an alginate compound are effected sequentially.

The present invention successfully addresses the shortcomings of the presently known configurations by providing a safe and effective pharmaceutical compositions and methods of use thereof for the treatment of hypoxia-related diseases.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF THE PREFERRED EMBODIMENTS

The present invention is of a pharmaceutical composition which includes as active ingredients TPEN and an alginate compound. The pharmaceutical composition can be used for the treatment of hypoxia-related diseases.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

U.S. Pat. No. 8,168,612 and U.S. patent application Ser. No. 12/530,488 teach the use of alginate compounds for the treatment of acute myocardial infarction (AMI). The therapeutic effect of alginate is attributed to the formation of a solid gel within the extra cellular matrix of the infarcted tissue, thereby providing mechanical support to the damaged heart tissue during its healing and repair processes following AMI. The prior art does not describe or suggest that alginate may exert biochemical of physiological activity that is therapeutically beneficial.

While reducing the present invention to practice, the present inventor has surprisingly uncovered that sodium alginate is capable of preventing hypoxia-induced injury to cultured cells. This finding was unexpected since a mechanical support could not be relevant to cultured cells and furthermore since alginate is not capable of penetrating inside living cells. Yet, as is illustrated in the Examples section hereinbelow, providing sodium alginate to cultured heart cells under hypoxia conditions resulted in substantial reduction in the amount of creatine kinase (CK) and lactate dehydrogenase (LDH) enzymes released by the cells. Since the release attenuation of these enzymes, (which are indicative of hypoxia injury), demand a biochemical pathway, it is assumed that the observed reduction in their release is an indication of the capability of alginate to protect cells from hypoxia injury via a biochemical route. The Examples further show that combining sodium alginate with TPEN resulted in a substantially more effective protection from hypoxia injury than with either compound alone.

Thus, according to one aspect of the present invention there is provided a pharmaceutical composition including N,N,N',N'-tetrakis-(2-pyridylmethyl)-ethylenediamine (TPEN) or a pharmaceutically acceptable salt thereof, an alginate compound, and a pharmaceutically acceptable carrier.

The phrase "pharmaceutical composition" used herein refers to a preparation of TPEN or a pharmaceutically acceptable salt thereof and an alginate compound as described herein with other chemical components such as pharmaceutically acceptable and suitable carriers and excipients. The purpose of a pharmaceutical composition is to facilitate administration of the active ingredients to a subject, or optionally to facilitate its application (contacting) in or on an inanimate object.

The term "pharmaceutically acceptable carrier" used herein refers to a carrier or a diluent that does not cause significant irritation to an organism and does not inhibit the distribution, therapeutic properties or otherwise does not abrogate the biological activity and properties of the administered or applied compound.

The term "excipient" used herein refers to an inert substance added to a pharmaceutical composition to further facilitate administration or application of a drug.

The term "TPEN" used herein refers to the compound N,N,N',N'-tetrakis-(2-pyridylmethyl)-ethylenediamine having the structure formula shown below.

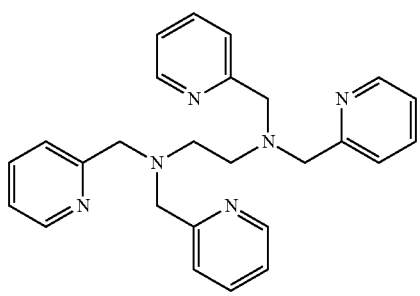 [SMILES: c1ccc(CN(CCN(Cc2ccccn2)Cc2ccccn2)Cc2ccccn2)nc1]

TPEN is readily available from several commercial manufacturers such as, for example, Sigma Aldrich Ltd, Germany.

The phrase "pharmaceutically acceptable salt" used herein refers to a charged species of the parent compound and its counter ion, which is typically used to modify the solubility characteristics of the parent compound and/or to reduce any significant irritation to an organism by the parent compound, while not abrogating the biological activity and properties of the administered compound. Examples, without limitation, of pharmaceutically acceptable salts include salts comprising an anion such as a carboxylate or sulfate anion, and/or a cation such as, but not limited to, ammonium, sodium, potassium and the like. Suitable salts are described in, e.g., Birge et al. (J. Pharm. Sci. 1977, 66:1-19).

In one embodiment of the present invention the final concentration of TPEN in the pharmaceutical composition ranges from about 1 to 50 µM. In another embodiment the final concentration of TPEN in the pharmaceutical composition ranges from about 0.1 to about 100 µM. In another embodiment the final concentration of TPEN in the pharmaceutical composition ranges from about 1 to about 10 µM. In another embodiment the final concentration of TPEN in the pharmaceutical composition ranges from about 3 to about 5 µM.

The phrase "alginate compound" used herein refers to a polyanionic polysaccharide copolymer derived from sea algae (e.g., *Laminaria hyperborea, L. digitata, Eclonia maxima, Macrocystis pyrifera, Lessonia nigrescens, Ascophyllum codosum, L. japonica, Durvillaea antarctica,* and *D. potatorum*) and which includes β-D-mannuronic (M) and α-L-guluronic acid (G) residues in varying proportions.

A suitable alginate compound, according to the teaching of the present invention, can be any biocompatible, non-immunogenic and, preferably, bio-erodible alginate compound.

In some embodiments, the alginate compound of the present invention has a monomer ratio between α-L-guluronic acid and β-D-mannuronic ranging between 1:1 to 3:1 and a molecular weight ranging between about 10 to about 300 kDa. In some embodiments the molecular weight of the alginate compound ranges between about 10 to about 50 kDa.

The alginate compound can be in a form of a free-base, an acid, a basic, an anion salt, or a monovalent cation salt. In some embodiments the alginate compound is a soluble alginate salt such as, but not limited to, sodium alginate, potassium alginate, lithium alginate, rubidium alginate and cesium salts of alginic acid, as well as the ammonium salt, and the soluble alginates of an organic base such as mono-, di-, or tri-ethanolamine alginates, aniline alginates, and the like.

In one embodiment the alginate compound is sodium alginate. Pharmaceutical grade sodium alginate which comply with all the quality and safety requirements of the European and United States of America (USA) pharmacological regulatory authorities, are readily available from several commercial manufacturers such as, for example, Novamatrix FMC Biopolymers (Drammen, Norway) or Qingdao Rongde Seaweed co., Ltd, (Qingdao, China).

In one embodiment the final concentration of the alginate compound in the pharmaceutical composition of the present invention ranges from about 0.1 to about 10% (w/v). In another embodiment the final concentration of the alginate compound in the pharmaceutical composition ranges from about 1 to about 4% (w/v). In another embodiment the final concentration of the alginate compound in the pharmaceutical composition is about 2% (w/v). In another embodiment the final concentration of the alginate compound in the pharmaceutical composition is about 1% (w/v).

Optionally, the pharmaceutical composition of the present invention further includes at least one therapeutic agent. Suitable therapeutic agents which may be included in the pharmaceutical composition of the present invention can be, for example, growth factors (e.g., basic fibroblast growth factor; bFGF), vascular endothelial growth factor (VEGF), insulin-like growth factor (IGF), members of the TGF-family, bone morphogenic proteins (BMP), platelet-derived growth factors, angiopoietins, and other factors such as myogenic factors, transcription factors, cytokines, and homeobox gene products, polynucleotides, polypeptides, hormones, anti-inflammatory drugs, anti-apoptotic drugs or antibiotic drugs.

Advantageously, the therapeutic agent or agents can be chemically linked to the alginate compound of the invention. Such linkage can be effected via any known chemical bonding approach, preferably a covalent bond. A suitable covalent bond can be, for example, an ester bond (e.g., a carboxylic ester bond, an oxyalkyl carboxylic ester bond, an amide bond, or a thioester bond), a glycosidic bond, a carbonate bond, a carbamate bond, a thiocarbamate bond, a urea bond or a thiourea bond.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the active ingredient(s) into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including transdermally, ophtalmically, vaginally, rectally, intranasally).

In one embodiment of the present invention the pharmaceutical composition is formulated as a solution suitable for injection or parenteral administration.

In another embodiment the pharmaceutical composition of the invention is formulated for topical administration.

In another embodiment the pharmaceutical composition of the invention is formulated for ophthalmic administration.

In another embodiment the pharmaceutical composition of the invention is formulated as eye drops.

The amount of the pharmaceutical composition to be administered or otherwise applied will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising active ingredient(s) according to embodiments of the invention formulated in a compatible pharmaceutical carrier may also be prepared, placed in an appropriate container, and labeled for treatment of a particular medical condition, disease or disorder, as is detailed herein.

According to some embodiments the pharmaceutical composition presented herein is packaged in a packaging material and identified in print, in or on the packaging material, for use in the treatment of hypoxia-related diseases.

As mentioned hereinabove the pharmaceutical composition of the present inventions can be used for protecting living cells and body tissues from hypoxia injury. Thus, according to one aspect of the present invention there is provided a method of treating a hypoxia-related disease. The method includes a step of administering to a subject in need thereof a therapeutically effective amount of the pharmaceutical composition of the present invention.

The term "hypoxia" used herein refers to an environment of oxygen deficiency or inadequate oxygen supply below physiological levels, such that the oxygen content ($O_2$) is less than or equal to about 5%. In most cases, hypoxic tissue will have an oxygen content that is less than or equal to about 2% or less. Hypoxia can be associated with low $O_2$ partial pressure ($pO_2$) less than 20 mm of mercury [mm Hg], such as less than 15 mmHg, less than 10 mm Hg, less than 5.0 mm Hg or less.

The phrase "hypoxia-related disease" used herein refers to a disease, disorder or condition where hypoxia in a tissue of the subject is involved. The hypoxia can either be a symptom or play a role in the cause, development, progression, amelioration, or cure of the disease, disorder or condition. Hypoxia-related disease can be, but not limited to, a disease, disorder or condition resulting from or associated with an ischemic-reperfusion injury.

A hypoxia-related disease according to the teachings of the present invention can be, but are not limited to, cardiovascular disease, ischemic heart disease, acute myocardial infarction (AMI), ischemic brain condition, ischemic stroke, macular degeneration, ocular ischemic syndrome, ischemic optic neuropathy (ION), diabetic retinopathy, arthritis, inflammation, sepsis, sepsis-induced shock, renal disease, tissue fibrosis, gastrointestinal disease, neurodegenerative disease, respiratory distress syndrome, bronchopulmonary displasia, pulmonary hypertension, hypoxic pulmonary hypertension, severe pulmonary hypertension, COPD, diabetic retinopathy, diabetes, corneal neovascularization, pathogenic blood vessel growth, musculoskeletal disorder, acute ischemic syndromes, myocardial hypoxia, cardiac hypertrophy, ischemic-reperfusion injury (IRI), IRI resulting from: cardiac heart surgery, coronary interventions (balloon and stent), arrhythmia management and organ transplantation, arrhythmias during angioplasty for coronary stent placement, or valvular interventions.

The phrase "treating" used herein refers to inhibiting, preventing or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The phrase "subject in need thereof" used herein refers to a mammalian male or female subject (e.g., human being) who is diagnosed with hypoxia-related disease. In a specific embodiment, this term encompasses individuals who are at risk to develop a hypoxia-related disease. Veterinary uses are also contemplated. The subject may be of any gender or at any age including neonatal, infant, juvenile, adolescent, adult and elderly adult.

The phrase "effective amount" used herein refers to an amount effective to provide a significant therapeutic benefit. The amount of a composition to be administered will, of course, be dependent on the subject being treated, the severity of the affliction, the manner of administration, the judgment of the prescribing physician, etc. An effective amount ranges from about 0.1 to about 10 ml (dwt between 1 and 1000 mg), preferably from about 1 to about 5 ml (dwt between 10 and 500 mg) of a concentration ranging between about 0.1 to about 10% (w/v), preferably between about 0.2 to about 5% (w/v), preferably between about 0.3 to about 2% (w/v), preferably between about 0.5 to about 1.5% (w/v), preferably about 2% (w/v), preferably about 1%.

The phrase "therapeutically effective amount" used herein refers to an amount effective to provide a significant therapeutic benefit. The amount of a composition to be administered will, of course, be dependent on the subject being treated, the severity of the affliction, the manner of administration, the judgment of the prescribing physician, etc. An effective amount ranges from about 0.1 to about 10 ml (dwt between 1 and 1000 mg), preferably from about 1 to about 5 ml (dwt between 10 and 500 mg) of a concentration ranging from about 0.1 to about 10% (w/v), preferably from about 0.2 to about 5% (w/v), preferably from about 0.3 to about 2% (w/v), preferably from about 0.5 to about 1.5% (w/v), preferably about 2%, preferably about 1% (w/v).

The pharmaceutical composition of the present invention can be used to treat a heart infarction by providing a subject in need thereof with a therapeutically effective amount of the pharmaceutical composition of the invention in or around the infarcted myocardium.

For treating acute myocardial infarction (AMI) the pharmaceutical composition can be administered intra-arterially, preferably intra-coronarily, via a suitable catheter such as a balloon catheter (see, for example, in Knight et al., Circulation 95:2075-2081, 1997).

The pharmaceutical composition of the present invention can be administered on the same day of the AMI during or after initiating reperfusion. In some embodiments the pharmaceutical composition is administered about one day after the AMI, in about one day after the AMI, in about two days after the AMI, in about three days after the AMI, in about four days after the AMI, in about five days after the AMI, in about six days after the AMI, or in about seven days after the AMI.

For treating ischemic stroke, the pharmaceutical composition of the present invention is preferably administered intra arterially via a suitable catheter. The administration can be effected at the commencement, during, or following reperfusion.

Such a catheter will typically comprise an elongated flexible catheter body containing one or more interior passageways (lumens), a proximal portion which allows material to be introduced into the catheter body and to flow through the lumen, a distal portion optionally having a tapered end and one or more exit ports at or near the end of the distal portion to permit material to exit the catheter in response to applied pressure.

Prior to or concomitantly with the injection of the pharmaceutical composition of the present invention, the ischemia-causing thrombus must be cleared via, for example, thrombolysis, mechanical recanalization or embolectomy.

Thrombolysis involves intravenously or intra-arterially administering plasminogen activators such as t-PA. Intra-arterial thrombolysis involves direct catheterization of an occluded artery and local administration of the thrombolytic agent via the catheter using procedures known in the art such as described, for example, in US Patent Publication No. 20080095760, Furlan et al. (JAMA 282:2003-11, 1999), Arnold et al. (J Neurol Neurosurg Psych 75:857-62, 2004) and Lindsberg and Mattle (Stroke 37:922-8, 2006).

Suitable mechanical re-canalization and embolectomy procedures are described, for example, by Bergui et al. (Stroke 37:145-50, 2006), Smith et al. (Stroke 36:1432-8, 2005) and U.S. Patent Application Nos. 20090105737 and 20050277979.

Delivering the pharmaceutical composition of the present invention to a precise desired location in cerebral artery, such as the site of occlusion causing the stroke, may be effected using procedures known in the art such are described, for example, in U.S. Pat. Nos. 4,995,862, 6,379,373 and U.S. Pat. Appl. Publication No. 20050228359.

The pharmaceutical composition of the present invention and a catheter suitable for administering thereof into a predetermined location within a cerebral artery may, if desired, be included in a kit which further comprises a packaging material identifying the pharmaceutical composition for use in the treatment of an ischemic brain condition.

The pharmaceutical composition of the present invention can also be used to treat diseases and conditions associated with an ischemic muscle tissue, such as an ischemic striated muscle tissue, by providing the ischemic muscle tissue with a therapeutically effective amount of the pharmaceutical composition.

The pharmaceutical composition of the present invention can also be used for protecting and preserving an extracorporeal tissue or organ from ischemia and oxygen radical-related damage, by immersing or bathing the extracorporeal tissue or organ or cell in an effective amount of the pharmaceutical composition.

Although the administration of TPEN and the alginate compound combined in a single pharmaceutical composition is preferred, the active ingredients of the present invention may be administered separately. Thus, the hypoxia-related disease can be treated by the steps of: (a) administering to a subject in need thereof a therapeutically effective amount of TPEN or a pharmaceutically acceptable salt thereof; and (b) administering to the subject a therapeutically effective amount of an alginate compound. In one embodiment steps (a) and (b) are effected concomitantly. In another embodiment steps (a) and (b) are effected sequentially.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Example 1

The Effect of TPEN and Sodium Alginate on the Amount of CK and LDH Released by Rat Primary Heart Cells Under Hypoxia Materials and Methods Compounds N,N,N',N'-tetrakis-(2-pyridylmethyl)-ethylenediamine (TPEN) was purchased from Sigma Aldrich, Germany.

Sodium alginate (UP-VLVG pharmaceutical grade, Mw=20-50 kDa) was purchased from Qingdao Rongde Seaweed co., Ltd, Qingdao, China.

Preparation of Rat Primary Heart Cells Cultures

Sprague Dawley rat hearts (1-2 days old) were sterilely removed and bathed three times in $Ca^{++}$ and $Mg^{++}$—free PBS to remove excess blood cells. The hearts were minced to small fragments and then agitated in a proteolytic enzyme-RDB solution (Life Science research, Inst., Nes Ziona, Israel) prepared from a fig tree extract as described previously (Brik et al., Basic Res. Cardiol. 85:237-246, 1990), Shneyvays et al., J Mol Cell Cardiol. 33:1249-1261, 2001). The RDB-solution was then diluted 1:200 in PBS at 25° C. for a few cycles of 10 min each. The supernatant suspension containing dissociated cells, to which medium containing 10% horse serum was added, was centrifuged at 500 g for 5 min. After centrifugation, the supernatant phase was discarded, and cells were re-suspended in Dulbecco's modified Eagle medium supplemented with 10% heat-inactivated horse serum and 0.5% chick embryo extract. Cell suspensions were diluted to $1\times10^6$ cells/ml, and 300 pl samples were placed in 24 well plates (4 plates) collagen/gelatin coated plastic culture dishes. A confluent monolayer, which exhibits spontaneous contractions in each well, developed in the culture within 2 days. The day after, Cells were washed to remove dead cells, and growth medium was replaced, as well as every 2 days and before experiment initiation, this time with glucose-free PBS. The experiments were then performed in vitro on these cardiomyocyte cultures after 5 days following the day of procedure beginning. Right before Hypoxia experiments, cultures wells were incubated in a humidified atmosphere incubator of 5% $CO_2$ and 95% air at 37° C. for 30 minute steady state.

Hypoxia Induction

Approximately $3\times10^5$ cardiomyocytes/well from neonatal rat hearts were cultured with glucose-free PBS and exposed to hypoxia (oxygen and glucose deprivation) for 180 min. using a procedure essentially as described by O. Golan et al. (Biochemical pharmacology, 81 (2011), pp. 1219-1227)

In brief, Hypoxia was performed in a closed chamber by replacement of air with 100% Argon. During hypoxia Oxygen levels in the $N_2$ atmosphere was below 1%. And after 180 min. of hypoxia, the pO2 in the PBS was <0.4 Torr. Hypoxic stress injury was determined based on the activity of lactate dehydrogenase (LDH) and creatine kinase (CK) released from the cells, at the end of 3 hr. hypoxic phase, and consequently after additional 2 hr. of reoxygenation.

Enzymes Release Measurement

For both LDH and CK measurements, 25 μL aliquots of each well incubated for 180 min under hypoxia, were transfer to clean 24 wells trays, which were placed within the automatic spectrophotometer and the product of the enzyme activity was measured through a wavelength of 340 nm at 30° C., under shaking. Results were expressed relatively to the control.

CK Activity Measurement

Creatine Kinase (CK) activity was determined within the cardiac cell medium (PBS) using CK-NAC Reagent (Creatine kinase, activated by N-acetyl cysteine) from Thermo Fisher Scientific Inc. Middletown, Va. 22645-1905 USA. Medium (PBS) samples (25 pl) were collected at the end of the hypoxic insult (after 180 min).

LDH Activity Measurement

Lactate dehydrogenase (LDH) activity was determined within the cardiac cell medium (PBS) using LDH-L kit (Thermo Trace, Melbourne, Australia). Medium (PBS) samples (25 pl) were collected at the end of the hypoxic insult (after 180 min).

Results

Tables 1-10 hereinbelow show that TPEN combined with sodium alginate effectively protected cultured heart cells from hypoxia injury.

Sodium alginate administered at concentrations of 0.3 and 1% to heart cells exposed to hypoxia resulted in 44.7 and 81.9% reduction of CK released from the cells, respectively (Table 1). The observed CK reduction is an indication that sodium alginate is capable of protecting cultured heart cells from hypoxia injury. This observation was highly surprising since the alginate molecule having a molecular weight of 20-50 kDa was not expected to be able to penetrate into the cultured cells or to interact therein.

Increasing sodium alginate concentration from 0.1 to 0.3% resulted in respective reductions of CK and LDH released from cells. For example, sodium alginate provided at concentrations of 0.1 and 0.3%, (combined with 3 μM TPEN) resulted in 65.5 and 74.3% CK reduction, respectively (Tables 2-3). Similarly, administering sodium alginate alone (without TPEN), at concentrations of 0.1 and 0.3%, resulted in CK reduction of 8.7 and 64.5%, respectively, and LDH reduction of 13.8 and 28.7%, respectively (Tables 7-9).

Administering TPEN at increasing concentrations from 0.3 to 3 μM resulted in respective reductions of CK and LDH released from the cells. For example, TPEN provided at 0.3, 1 and 3 μM (combined with 0.1% sodium alginate) resulted in 20.5, 60.8 and 65.5% of CK reduction, respectively (Table 2). However, the TPEN effect on CK and LDH reduction was declining when TPEN was administered at above-optimal concentrations. For example, TPEN administered at 7.5 μM (combined with 0.1% sodium alginate) resulted in CK reduction of just 46.2%, compared with a 65.5% CK reduction resulted from administering TPEN at a concentration of 3 μM (combined with 0.1% sodium alginate; Table 2).

Interestingly, the declining efficacy of TPEN when administered at the above-optimal concentration was overridden by increasing the amount of sodium alginate. Accordingly, TPEN administered at a concentration of 7.5 μM, combined with sodium alginate at a concentration of 0.3% resulted in 71.2% CK reduction (Table 3).

Hence, the results indicate that the use of TPEN combined with sodium alginate is substantially superior to the use of either compound alone in protecting heart cells from hypoxia injury.

TABLE 1

The effect of sodium alginate on the amount of CK released from rat heart cells under hypoxia*

| Environment* | Sodium Alginate (%) | Mean | SD | CK Reduction (%)** |
|---|---|---|---|---|
| Hypoxia* | 1 | 0.0064 | 0.0011 | 81.9 |
| Hypoxia* | 0.3 | 0.0099 | 0.0023 | 44.7 |
| Hypoxia* | 0.1 | 0.0143 | 0.0019 | -2.1 |
| Hypoxia* | 0 | 0.0141 | 0.0011 | n/a |
| Control (Normoxia) | 0 | 0.0047 | 0.0008 | n/a |

*Cells were exposed to hypoxia for 3 hours.

**Values are calculated as follows: [(measured CK activity in treated cell culture) − (measured CK activity in untreated cell culture)]/[(measured CK activity in untreated cell culture) − ([(measured CK activity in control cell culture not exposed to hypoxia)] × 100.

TABLE 2

The effect of sodium alginate and TPEN on the amount of CK released from rat heart cells under hypoxia*

| Environment* | Sodium Alginate (%) | TPEN (μM) | Mean | SD | CK Reduction (%)** |
|---|---|---|---|---|---|
| Control (normoxia) | 0 | 0 | 0.0039 | 0.0018 | n/a |
| Hypoxia | 0 | 0 | 0.0610 | 0.0093 | n/a |
| Hypoxia | 0.1 | 0 | 0.0578 | 0.0094 | 5.6 |
| Hypoxia | 0.1 | 0.3 | 0.0493 | 0.0122 | 20.5 |
| Hypoxia | 0.1 | 1 | 0.0263 | 0.0052 | 60.8 |
| Hypoxia | 0.1 | 3 | 0.0236 | 0.0124 | 65.5 |
| Hypoxia | 0.1 | 7.5 | 0.0346 | 0.0031 | 46.2 |

*Cells were exposed to hypoxia for 3 hours.

**Values are calculated as follows: [(measured CK activity in treated cell culture) − (measured CK activity in untreated cell culture)]/[(measured CK activity in untreated cell culture) − ([(measured CK activity in control cell culture not exposed to hypoxia)] × 100.

TABLE 3

The effect of sodium alginate and TPEN on the amount of CK released from rat heart cells under hypoxia*

| Environment* | Sodium Alginate (%) | TPEN (μM) | Mean | SD | CK Reduction (%)** |
|---|---|---|---|---|---|
| Control (normoxia) | 0 | 0 | 0.0039 | 0.0018 | n/a |
| Hypoxia | 0 | 0 | 0.0587 | 0.0118 | n/a |
| Hypoxia | 0.3 | 0 | 0.0418 | 0.0075 | 30.8 |
| Hypoxia | 0.3 | 0.3 | 0.0341 | 0.0080 | 44.9 |
| Hypoxia | 0.3 | 1 | 0.0223 | 0.0079 | 66.4 |
| Hypoxia | 0.3 | 3 | 0.0180 | 0.0044 | 74.3 |
| Hypoxia | 0.3 | 7.5 | 0.0197 | 0.0084 | 71.2 |

*Cells were exposed to hypoxia for 3 hours.

**Values are calculated as follows: [(measured CK activity in treated cell culture) − (measured CK activity in untreated cell culture)]/[(measured CK activity in untreated cell culture) − ([(measured CK activity in control cell culture not exposed to hypoxia)] × 100.

TABLE 4

The effect of sodium alginate and TPEN on the release of LDH from rat heart cells under hypoxia*

| Environment* | Sodium Alginate (%) | TPEN (μM) | Mean | SD | LDH Reduction (%)** |
|---|---|---|---|---|---|
| Control (normoxia) | 0 | 0 | 0.0068 | 0.0056 | n/a |
| Hypoxia | 0 | 0 | 0.0642 | 0.0187 | n/a |
| Hypoxia | 1 | 0 | 0.0135 | 0.0031 | 88.3 |
| Hypoxia | 1 | 0.3 | 0.0140 | 0.0012 | 87.5 |
| Hypoxia | 1 | 1 | 0.0132 | 0.0010 | 88.9 |
| Hypoxia | 1 | 3 | 0.0109 | 0.0021 | 92.9 |
| Hypoxia | 1 | 7.5 | 0.0174 | 0.0034 | 81.5 |

*Cells were exposed to hypoxia for 3 hours.

**Values are calculated as follows: [(measured LDH activity in treated cell culture) − (measured LDH activity in untreated cell culture)]/[(measured LDH activity in untreated cell culture) − ([(measured LDH activity in control cell culture not exposed to hypoxia)] × 100.

TABLE 5

The effect of sodium alginate and TPEN on the amount of LDH released from rat heart cells under hypoxia*

| Environment* | Sodium Alginate (%) | TPEN (μM) | Mean | SD | LDH Reduction (%)** |
|---|---|---|---|---|---|
| Control (normoxia) | 0 | 0 | 0.0039 | 0.0018 | n/a |
| Hypoxia | 0 | 0 | 0.0610 | 0.0093 | n/a |
| Hypoxia | 0.1 | 0 | 0.0578 | 0.0094 | 5.6 |
| Hypoxia | 0.1 | 0.3 | 0.0493 | 0.0122 | 20.5 |
| Hypoxia | 0.1 | 1 | 0.0263 | 0.0052 | 60.8 |
| Hypoxia | 0.1 | 3 | 0.0236 | 0.0124 | 65.5 |
| Hypoxia | 0.1 | 7.5 | 0.0346 | 0.0031 | 46.2 |

*Cells were exposed to hypoxia for 3 hours.

**Values are calculated as follows: [(measured LDH activity in treated cell culture) − (measured LDH activity in untreated cell culture)]/[(measured LDH activity in untreated cell culture) − ([(measured LDH activity in control cell culture not exposed to hypoxia)] × 100.

TABLE 6

The effect of sodium alginate and TPEN on the amount of LDH released from rat heart cells under hypoxia*

| Environment* | Sodium Alginate (%) | TPEN (μM) | Mean | SD | LDH Reduction (%)** |
|---|---|---|---|---|---|
| Control (normoxia) | 0 | 0 | 0.0039 | 0.0018 | n/a |
| Hypoxia | 0 | 0 | 0.0587 | 0.0118 | n/a |
| Hypoxia | 0.3 | 0 | 0.0418 | 0.0075 | 30.3 |
| Hypoxia | 0.3 | 0.3 | 0.0287 | 0.0125 | 54.7 |
| Hypoxia | 0.3 | 1 | 0.0223 | 0.0079 | 66.4 |
| Hypoxia | 0.3 | 3 | 0.0180 | 0.0044 | 74.3 |
| Hypoxia | 0.3 | 7.5 | 0.0230 | 0.0065 | 65.0 |

*Cells were exposed to hypoxia for 3 hours.

**Values are calculated as follows: [(measured LDH activity in treated cell culture) − (measured LDH activity in untreated cell culture)]/[(measured LDH activity in untreated cell culture) − ([(measured LDH activity in control cell culture not exposed to hypoxia)] × 100.

TABLE 7

The effect of sodium alginate and TPEN on the amount of CK released from rat heart cells under hypoxia*

| Environment* | Sodium Alginate (%) | TPEN (µM) | Mean | SD | CK Reduction (%)** |
|---|---|---|---|---|---|
| Control (normoxia) | 0 | 0 | 0.0052 | 0.0019 | n/a |
| Hypoxia | 0 | 0 | 0.0750 | 0.0060 | n/a |
| Hypoxia | 0.1 | 0 | 0.0685 | 0.0026 | 8.7 |
| Hypoxia | 0 | 1 | 0.0643 | 0.0171 | 14.3 |
| Hypoxia | 0.1 | 1 | 0.0605 | 0.0124 | 19.3 |
| Hypoxia | 0.3 | 1 | 0.0358 | 0.0123 | 52.3 |

*Cells were exposed to hypoxia for 3 hours.
**Values are calculated as follows: [(measured CK activity in treated cell culture) − (measured CK activity in untreated cell culture)]/[(measured CK activity in untreated cell culture) − ([(measured CK activity in control cell culture not exposed to hypoxia)] × 100.

TABLE 8

The effect of sodium alginate and TPEN on the amount of CK released from rat heart cells under hypoxia*

| Environment* | Sodium Alginate (%) | TPEN (µM) | Mean | SD | CK Reduction (%)** |
|---|---|---|---|---|---|
| Control (normoxia) | 0 | 0 | 0.0052 | 0.0019 | n/a |
| Hypoxia | 0 | 0 | 0.0770 | 0.0182 | n/a |
| Hypoxia | 0.3 | 0 | 0.0468 | 0.0068 | 64.5 |
| Hypoxia | 0 | 0.3 | 0.0411 | 0.0192 | 46.6 |
| Hypoxia | 0.3 | 0.3 | 0.0192 | 0.0077 | 75.1 |
| Hypoxia | 0.1 | 0 | 0.0160 | 0.0047 | 79.2 |
| Hypoxia | 0.1 | 0.3 | 0.0187 | 0.0090 | 74.7 |

*Cells were exposed to hypoxia for 3 hours.
**Values are calculated as follows: [(measured CK activity in treated cell culture) − (measured CK activity in untreated cell culture)]/[(measured CK activity in untreated cell culture) − ([(measured CK activity in control cell culture not exposed to hypoxia)] × 100.

TABLE 9

The effect of sodium alginate and TPEN on the amount of LDH released from rat heart cells under hypoxia*

| Environment* | Sodium Alginate (%) | TPEN (µM) | Mean | SD | LDH Reduction (%)** |
|---|---|---|---|---|---|
| Control (normoxia) | 0 | 0 | 0.0096 | 0.0071 | n/a |
| Hypoxia | 0 | 0 | 0.0719 | 0.0036 | n/a |
| Hypoxia | 0.1 | 0 | 0.0620 | 0.0044 | 13.8 |
| Hypoxia | 0 | 1 | 0.0647 | 0.0178 | 10.0 |
| Hypoxia | 0.1 | 1 | 0.0647 | 0.0117 | 10.0 |
| Hypoxia | 0.3 | 1 | 0.0298 | 0.0062 | 58.6 |

*Cells were exposed to hypoxia for 3 hours.
**Values are calculated as follows: [(measured LDH activity in treated cell culture) − (measured LDH activity in untreated cell culture)]/[(measured LDH activity in untreated cell culture) − ([(measured LDH activity in control cell culture not exposed to hypoxia)] × 100.

TABLE 10

The effect of sodium alginate and TPEN on the amount of LDH released from rat heart cells under hypoxia*

| Environment* | Sodium Alginate (%) | TPEN (µM) | Mean | SD | LDH Reduction (%)** |
|---|---|---|---|---|---|
| Control (normoxia) | 0 | 0 | 0.0096 | 0.0071 | n/a |
| Hypoxia | 0 | 0 | 0.0676 | 0.0226 | n/a |
| Hypoxia | 0.3 | 0 | 0.0482 | 0.0061 | 28.7 |
| Hypoxia | 0 | 0.3 | 0.0409 | 0.0105 | 39.5 |
| Hypoxia | 0.3 | 0.3 | 0.0245 | 0.0105 | 63.8 |
| Hypoxia | 0.1 | 0 | 0.0158 | 0.0057 | 76.7 |
| Hypoxia | 0.1 | 0.3 | 0.0352 | 0.0218 | 47.9 |

*Cells were exposed to hypoxia for 3 hours.
**Values are calculated as follows: [(measured LDH activity in treated cell culture) − (measured LDH activity in untreated cell culture)]/[(measured LDH activity in untreated cell culture) − ([(measured LDH activity in control cell culture not exposed to hypoxia)] × 100.

Example 2

Intra-coronary Administration of TPEN and Sodium Alginate to Infarcted Myocardium Tissue-induced Dogs Material and Methods Test Compositions:

The test compositions are: saline (negative control) and a TPEN/Alginate solution composed of 3 µM TPEN and 1% (w/v) sodium alginate (UP-VLVG, Mw 20-50 kDa) in saline.

Induction of Acute Myocardial Infarction (AMI)

Two years old (20-25 kg) dogs are anesthetized and intubated and respired with room air. Animals are sedated with intravenous oxymorphone hydrochloride (0.22 mg/kg) and diazepam (0.17 mg/kg) and a plane of anesthesia is maintained with 1-2% isofluorane. The procedures are performed with the chest closed and under sterile conditions. To produce the coronary occlusion, a 2.7 French PTCA balloon catheter is advanced introduced over a 0.014 inch wire through a 4 JL guiding catheter through a femoral arteriotomy. A 4.0 mm diameter, 15 mm balloon is used. The guiding catheter and positioned in the Left Main coronary artery and the wire, advanced under fluoroscopic guidance, is positioned in the distal Circumflex coronary artery. The balloon catheter is advanced into the coronary artery over the wire and positioned proximal to the first marginal branch. In all instances, the animals are anti-coagulated with 750-1000 USP units of intravenous sodium heparin.

Intra-coronary Administration

Once in place, the PTCA balloon is inflated to occlude the coronary artery. Complete occlusion of the coronary artery is confirmed by ST-segment elevation on the electrocardiogram and near absence of LV posterior wall motion assessed by transthoracic 2-dimensional echocardiography. In all instances, the coronary occlusion is maintained for 3 to 5 hours. At the end of the occlusion, the balloon is deflated to allow for coronary reperfusion.

The test solution (2 ml volume) is injected into the animals' Circumflex coronary artery. To simulate the likely clinical setting for use of the test solution, the coronary injection of the test solution is made either on the same day of the AMI (about one hour following initiating reperfusion), or 2-5 days following the AMI. Dogs are randomly assigned to receive any of the test solution. All animals are followed for 4 months following the AMI. Angiographic and echocardiographic measurements are made at baseline, prior to inducing the AMI, just prior to administering the test solutions and at two and four months thereafter.

End Points

1. Prevention or attenuation of progressive LV dilation based on ventriculographic measurements of LV end-systolic and end-diastolic volume.

2. Prevention of progressive deterioration of LV systolic function based on ventriculographic measurement of LV ejection fraction (EF) and echocardiographic measurement of LV fractional area of shortening (FAS).

3. Prevention or attenuation of infarct expansion based on echocardiographic measurements of systolic thickening of the infarcted LV wall.

Angiographic and Echocardiographic Measurements

All angiographic and echocardiographic measurements are made during cardiac catheterization under general anesthesia and sterile conditions. Left ventriculograms are obtained with the dog placed on its right side and digitally recorded during the injection of 20 ml of contrast material (RENO-M-60 Squibb, Princeton, N.J.). Correction for image magnification is made with a radiopaque calibrated grid placed at the level of the LV. LV end-systolic (ESV) and end-diastolic (EDV) volumes are calculated from LV silhouettes using the area-length method (Dodge et al., Am J Cardiol. 1966; 18:10-24, 1966). Left ventricular EF is calculated as the ratio of the difference of EDV and ESV to EDV times 100 (Sabbah et al., Circulation 89:2852-2859, 1994).

All 2-dimensional echocardiographic measurements are made with the dog placed in the right lateral decubitus position. Echocardiographic studies are performed using a General Electric VIVID 7 Dimension ultrasound system with a 3.5 MHz transducer and recorded on a Mitsubishi MD3000 VHS recorder for off-line analysis. A LV short-axis view at mid-papillary muscle level is recorded and used to calculate the percent fractional shortening (FAS; Kono et al. J Am Coll Cardiol 1992; 19:1101-1105, 1992), defined as the difference between the end-diastolic area and the end-systolic area divided by the end-diastolic area times 100. Percent systolic wall thickening of the LV anterior wall, posterior wall and inter-ventricular septum are also measured using the short axis view and each calculated as the ratio of wall thickness at end-diastole to wall thickness at end-systole divided by wall thickness at end-diastole times 100. Extrasystolic and post-extrasystolic beats are excluded from all analysis.

Statistical Analysis

Within group angiographic and echocardiographic data are analyzed using repeated measures analysis of variance (ANOVA) with alpha set at 0.05. If the overall ANOVA is significant, then pairwise comparisons between pre-treatment (PRE) and 2 and 4 months are performed using the Student-Newman-Keuls test. For this test a p-value lower than 0.05 is considered significant. To assess treatment effect, the change ($\Delta$) in each measure from PRE to 2 months and PRE to 4 months post-treatment is calculated for each of the two study arms. To determine whether significant differences in $\Delta$ were present between the control groups and the TPEN/alginate treated group, a t-statistic for two means is used with $p<0.05$ considered significant.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition, consisting of 1-10 µM of N,N,N',N'-tetrakis-(2-pyridylmethyl)-ethylenediamine (TPEN) or a pharmaceutically acceptable salt thereof, a 10-50 kDa alginate compound in an amount of 0.1 to about 1% (w/v), and a pharmaceutically acceptable carrier.

2. The pharmaceutical composition of claim 1, wherein said alginate compound is sodium alginate.

3. The pharmaceutical composition of claim 1, wherein the concentration of said alginate compound in the pharmaceutical composition is about 1% (w/v).

4. The pharmaceutical composition of claim 1, wherein the concentration of said TPEN in the pharmaceutical composition ranges from 3 to 5 µM.

5. The pharmaceutical composition of claim 1, wherein a monomer ratio between α-L-guluronic acid and β-D-mannuronic acid in said alginate compound ranges between 1:1 and 3:1.

6. A method for inhibiting or arresting the development of acute myocardial infarction or causing the reduction, remission, or regression of acute myocardial infarction, comprising administering to a patient suffering from acute myocardial infarction a therapeutically effective amount of the pharmaceutical composition of claim 1 to treat acute myocardial infarction in the patient.

7. The method of claim 6, wherein said administering is effected via intravenous injection, intravenous drip, or catheterization.

8. The method of claim 7, wherein said administering is effected via intra-arterial catheterization.

9. The method of claim 6, wherein said therapeutically effective amount is in a range of about 0.1 to about 10 ml of the pharmaceutical composition.

10. The method of claim 6, wherein said administration is effected on the same day of occurrence of the acute myocardial infarction in the subject.

11. A method for inhibiting or arresting the development of ischemic stroke or causing the reduction, remission, or regression of ischemic stroke, comprising administering to a patient suffering from ischemic stroke a therapeutically effective amount of the pharmaceutical composition of claim 1 to treat ischemic stroke in the patient.

12. The method of claim 11, wherein said administering is effected via injection or catheterization.

13. The method of claim 12, wherein said administering is effected via intra-arterial catheterization.

14. The method of claim 11, wherein said therapeutically effective amount is in a range of about 0.1 to about 10 ml of the pharmaceutical composition.

* * * * *